US007947283B2

(12) United States Patent
Tu et al.

(10) Patent No.: US 7,947,283 B2
(45) Date of Patent: May 24, 2011

(54) COMPOSITIONS AND METHODS FOR TREATING PSORIASIS BY *GANODERMA LUCIDUM* (REISHI) POLYSACCHARIDES

(75) Inventors: Tseng-Rong Tu, Taitung (TW);
Chia-Feng Li, Caotun Township (TW);
Sung-Hsieh Su, Taipei (TW); Chi-Huey Wong, La Jolla, CA (US); Eugene Fan, La Jolla, CA (US)

(73) Assignees: Wyntek Corporation, Taipei (TW);
Academia Sinica, Taipei (TW)

( * ) Notice: Subject to any disclaimer, the term of this patent is extended or adjusted under 35 U.S.C. 154(b) by 155 days.

(21) Appl. No.: 12/231,112

(22) Filed: Aug. 29, 2008

(65) Prior Publication Data
US 2009/0060940 A1 Mar. 5, 2009

Related U.S. Application Data

(60) Provisional application No. 60/969,107, filed on Aug. 30, 2007.

(51) Int. Cl.
*A01N 65/00* (2009.01)
*A61K 36/074* (2006.01)
(52) U.S. Cl. .................................. 424/195.15; 514/863
(58) Field of Classification Search ........................ None
See application file for complete search history.

(56) References Cited

U.S. PATENT DOCUMENTS

| 4,522,811 | A | | 6/1985 | Eppstein et al. |
| 5,334,704 | A | | 8/1994 | Tsunoo et al. |
| 5,863,769 | A | * | 1/1999 | Young |
| 5,997,875 | A | * | 12/1999 | Zhou et al. |
| 6,395,310 | B1 | | 5/2002 | Iwasaki |
| 6,464,982 | B1 | | 10/2002 | Lam |
| 6,471,860 | B1 | | 10/2002 | Miltenyi et al. |
| 6,613,754 | B1 | | 9/2003 | Wu |
| 7,135,183 | B1 | | 11/2006 | Wang et al. |
| 7,323,176 | B2 | | 1/2008 | Wang et al. |
| 2003/0095981 | A1 | | 5/2003 | Wong et al. |
| 2003/0068329 | A1 | | 10/2003 | Kosuna et al. |
| 2005/0180988 | A1 | * | 8/2005 | Chung et al. |
| 2007/0104729 | A1 | | 5/2007 | Wang et al. |
| 2007/0105814 | A1 | | 5/2007 | Hua et al. |
| 2007/0231339 | A1 | | 10/2007 | Yu et al. |
| 2008/0214442 | A1 | | 9/2008 | Yu et al. |
| 2008/0247989 | A1 | | 10/2008 | Shih et al. |

FOREIGN PATENT DOCUMENTS

| WO | WO/2006/044616 | 4/2006 |
| WO | WO/2007/047021 | 4/2007 |
| WO | WO/2008/036421 | 3/2008 |

OTHER PUBLICATIONS

Blomberg K. et al., *Fluorescent europium chelates as target cell markers in the assessment of natural killer cell cytotoxicity*, J. Immunol. Methods, 1993, vol. 160, pp. 27-34.

Bowden, R. et al., *Alteration of Cytokine Levels in Murine Retrovirus Infection: Modulation by Combination Therapy*, International Journal of Immunopharmacology 1999, vol. 21, pp. 815-827.
Braciale T. et al., *Antigen presentation: structural themes and functional variations*, Immunology Today, 1991, vol. 12, No. 4, pp. 124-129.
Bronte V. et al., *IL-2 Enhances the Function of Recombinant Poxvirus-Based Vaccines in the Treatment of Established Pulmonary Metastases*, J. Immunol., 1995, vol. 154, pp. 5282-5292.
Chen H. et al., *Studies on the immuno-modulating and anti-tumor activities of Ganoderma lucidum (Reishi) polysaccharides*, Bioorg. Med. Chem., 2004, vol. 12, pp. 5595-5601.
Chen-Bettecken U. et al., *IgM RNA switch from membrane to secretory form is prevented by adding antireceptor antibody to bacterial lipopolysaccharide-stimulated murine primary B-cell cultures*, Proc. Natl. Acad. Sci., USA, 1985, vol. 82, pp. 7384-7388.
Chien C., *Polysaccharides of Ganoderma lucidum alter cell immunophenotypic expression and enhance $CD56^+$ NK-cell cytotoxicity in cord blood*, Bioorg. Med. Chem., 2004, vol. 12, pp. 5603-5609.
Feltkamp M. et al., *Cytotoxic T lymphocytes raised against a subdominant epitope offered as a synthetic peptide eradicate human papillomavirus type 16-induced tumors*, Eur. J. Immunol., 1995, vol. 25, pp. 2638-2642.
Franz, G., *Polysaccharides in Pharmacy: Current Applications and Future Concepts*, Planta Medica, 1989, vol. 55, pp. 493-497.
Furusawa, E. et al., *Antitumor Activity of Ganoderma lucidum, an Edible Mushroom, on Intraperitoneally Implanted Lewis Lung Carcinoma in Synergenic Mice*, Phytotherapy Research, vol. 6, 1992, pp. 300-304.
Grohmann U. et al, $CD8^+$ *cell activation to a major mastocytoma rejection antigen, P815AB: requirement for tumor helper peptides in priming for skin test reactivity to a P815AB-related peptide*, Eur. J. Immunol., 1995, vol. 25, pp. 2797-2802.
Halhoul M. et al., *Differential Determination of Glucose and Fructose, and Glucose- and Fructose-Yielding Substances with Anthrone*, Anal. Biochem., 1972, vol. 50, pp. 337-343.
Hellman M. et al., *Separation of Isomeric Polyphenyls by Adsorption Chromatography*, 1990, Analytical Chemistry, pp. 1206-1210.
Henderson R. et al., *Human Tumor Antigens are Ready to Fly*, Advances in Immunology, 1996, vol. 62, pp. 217-256.
Hsu H. et al., *Extract of Reishi Polysaccharides Induces Cytokine Expression via TLR4-Modulated Protein Kinase Signaling Pathways*, J. Immunol., 2004, vol. 173, pp. 5989-5999.

(Continued)

Primary Examiner — Michele Flood
(74) Attorney, Agent, or Firm — Eckman Basu LLP

(57) ABSTRACT

A method for treating psoriasis by providing a pharmaceutical composition containing at least *Ganoderma lucidum* extract and administering a therapeutically effective amount of the composition to a patient in need thereof. Also disclosed is a method for treating psoriasis by first purifying *Ganoderma lucidum* extract into at least one fraction, then providing a pharmaceutical composition comprising at least one of the *Ganoderma lucidum* fractions, and administering a therapeutically effective amount of the composition to a patient in need thereof. A method for alleviating symptoms of psoriasis is disclosed. The symptoms of psoriasis are alleviated by providing a pharmaceutical composition containing at least *Ganoderma lucidum* extract and administering an amount of the composition effective to increase at least one of an IL-10 and IL-1Ra expression, whereby the symptoms of psoriasis are ameliorated.

Figure 1A:

11 Claims, 2 Drawing Sheets
(2 of 2 Drawing Sheet(s) Filed in Color)

OTHER PUBLICATIONS

Jermyn M., *Increasing the Sensitivity of the Anthrone Method for Carbohydrate*, Anal. Biochem., 1975, vol. 68, pp. 332-335.

Kim B. et al., *Antineoplastic Components of Korean Basidomycetes*, Korean Journal of Mycology, 1980, vol. 8, No. 2, pp. 107-114.

Kovacsovics-Bankowski M. et al., *A Phagosome-to-Cytosol Pathway for Exogenous Antigens Presented on MHC Class I Molecules*, Science, 1995, vol. 267, pp. 243-246.

Lin K. et al., *Reishi Polysaccharides Induce Immunoglobulin Production through the TLR4/TLR2-mediated Induction of Transcription Factor Blimp-1*, J. Biol. Chem., 2006, vol. 281, No. 34, pp. 24111-24123.

Lo C. et al., *Simple fractionation of phospholipase $A_2$ analogues from snake venom by high-performance liquid chromatography*, J. Chromatogr. 1990, vol. 530, pp. 129-136.

Miyazaki, T. et al., *Structural Examination of an Alkali-Extracted, Water-Soluble Heteroglycan of the Fungus Ganoderma lucidum*, Carbohydrate Research, 1982, vol. 109, pp. 290-294.

Mizuno et al., *Fractionation, Chemical Modification and Antitumor Activity of Water-insoluble Polysaccharides of the Fruiting Body of Ganoderma lucidum*, Journal of the Agricultural Chemical Society of Japan (Nippon Nôgeikagaku Kaishi), 1985, vol. 59, No. 11, pp. 1143-1151. [English language abstract enclosed].

Mosmann, T., *Rapid Colorimetric Assay for Cellular Growth and Survival: Application to Proliferation and Cytotoxicity Assays*, Journal of Immunological Methods, 1983, vol. 65, pp. 55-63.

Müller A. et al., *Receptor Binding and Internalization of a Water-Soluble (1→3)-β-D-Glucan Biologic Response Modifier in Two Monocyte/Macrophage Cell Lines*, J. Immunol., 1996, vol. 156, pp. 3418-3425.

Murphy, E. et al., *Detection of in vivo expression of interleukin-10 using a semi-quantitative polymerase chain reaction method in Schistosoma mansoni Infected Mice*, Journal of Immunological Methods, 1993, vol. 162, pp. 211-223.

Norkin L. et al., *Association of Caveolin with Chlamydia trachomatis Inclusions at Early and Late Stages of Infection*, Exp. Cell. Res., 2001, vol. 266, pp. 229-238.

Puccetti P. et al., *Use of a skin test assay to determine tumor-specific $CD8^+$ T cell reactivity*, Eur. J. Immuno., 1994, vol. 24, pp. 1446-1452.

Robbins P. et al., *A Mutated β-Catenin Gene Encodes a Melanoma-specific Antigen Recognized by Tumor Infiltrating Lymphocytes*, J. Exp. Med., 1996, vol. 183, pp. 1185-1192.

Sanchez, J. et al., *The mouse SWISS-2D PAGE database: a tool for proteomics study of diabetes and obesity*, Proteomics, 2001, vol. 1, pp. 136-163.

Shaffer A., *XBP1, Downstream of Blimp-1, Expands the Secretory Apparatus and Other Organelles, and Increases Protein Synthesis in Plasma Cell Differentiation*, Immunity, 2004, vol. 21, pp. 81-93.

Shao B. et al., *Immune receptors for polysaccharides from Ganoderma lucidum*, Biochem. Biophys. Res. Commun., 2004, vol. 323, pp. 133-141.

Shapiro-Shelef M. et al., *Blimp-1 Is Required for the Formation of Immunoglobulin Secreting Plasma Cells and Pre-Plasma Memory B Cells*, Immunity, 2003, vol. 19, pp. 607-620.

Shiao M. et al., *Natural Products and Biological Activities of the Chinese Medicinal Fungus Ganoderma lucidum*, American Chemical Society, 1994, pp. 342-354.

Sieckmann D. et al., *Activation of Mouse Lymphocytes by Anti-Immunoglobulin*, J. Exp. Med., 1978, vol. 147, pp. 814-829.

Smith J. et al., *Current Protocols in Molecular Biology*, John Wiley & Sons, Inc., 2005, Sec. 11.1-11.3.

Somani B. et al., *A Modified Anthrone-Sulfuric Acid Method for the Determination of Fructose in the Presence of Certain Proteins*, Anal. Biochem., 1987, vol. 167, p. 327-330.

Sone Y. et al. *Structures and Antitumor Activities of the Polysaccharides Isolated from Fruiting Body and the Growing Culture of Mycelium of Ganoderma lucidum*, Agric. Biol. Chem., 1985, vol. 49, pp. 2641-2653.

Spackman D. et al., *Automatic Recording Apparatus for Use in the Chromatography of Amino Acids* Anal. Chem., 1958, vol. 30, pp. 1190-1206.

Usui, T. et al. *Isolation and characterization of antitumor active β-D-glucans from the fruit bodies of Ganoderma applanatum*, Carbohydrate Research, 1983, vol. 115, pp. 273-280.

Van Strijp J. et al., *Ligand Specificity of Purified Complement Receptor Type Three (CD11b/CD18, $^\alpha m^\beta 2$, Mac-1)*, J. Immunol., 1993, vol. 151, pp. 3324-3336.

Větvička V. et al., *Soluble β-Glucan Polysaccharide Binding to the Lectin Site of Neutrophil or Natural Killer Cell Complement Receptor Type 3 (CD11b/CD18) Generates a Primed State of the Receptor Capable of Mediating Cytotoxicity of iC3b-Opsonized Target Cells*, J. Clin. Invest., 1996, vol. 98, pp. 50-61.

Vitiello A. et al., *Development of a Lipopeptide-based Therapeutic Vaccine to Treat Chronic HBV Infection*, J. Clin. Inv. 1995, vol. 95, pp. 341-349.

Wang S. et al., *The Anti-Tumor Effect of Ganoderma lucidum is Mediated by Cytokines Released from Activated Macrophages and T. Lymphocytes*, Int. J. Cancer, 1997, vol. 70, pp. 699-705.

Wang Y. et al., *Studies on the Immuno-Modulating and Antitumor Activities of Ganoderma lucidum (Reishi) Polysaccharides: Functional and Proteomic Analyses of a Fucose-Containing Glycoprotein Fraction Responsible for the Activities*, Bioorg. Med. Chem., 2002, vol. 10, pp. 1057-1062.

Widmann C. et al., *T helper epitopes enhance the cytotoxic response of mice immunized with MHC class I-restricted malaria peptides*, J. Immunol. Methods, 1992, vol. 155, pp. 95-99.

York I. et al., *Antigen Processing and Presentation by the Class I Major Histocompatibility Complex*, Annu. Rev. Immunol., 1996, vol. 14, pp. 369-396.

Zhang J. et al., *Activation of B lymphocytes by GLIS, a bioactive proteoglycan from Ganoderma lucidum*, Life Sci., 2002, vol. 71, pp. 623-638.

Asadullah, K. et al., *Interleukin-10 and Psoriasis*, Interleukin-10, 2006, pp. 161-168.

Raj, D. et al., *Keratinocyte Apoptosis in Epidermal Development and Disease*, J. Investigative Dermatology, 2006, vol. 126, pp. 243-257.

* cited by examiner

COMPOSITIONS AND METHODS FOR TREATING PSORIASIS BY *GANODERMA LUCIDUM* (REISHI) POLYSACCHARIDES

RELATED APPLICATIONS

The present disclosure incorporates by reference and claims the Paris Convention Priority of U.S. Provisional Application Ser. No. 60/969,107, filed on Aug. 30, 2007, entitled "Compositions and Methods for Treating Psoriasis By *Ganoderma Lucidum* (Reishi) Polysaccharides."

BACKGROUND

Psoriasis is a chronic recurring skin disease, often characterized with red or silvery white scaly patches known as psoriatic plaques. These patches are due to inflammation and excessive skin production. Plaques commonly occur on the elbows and knees of patients, though any area of the body may be affected. Psoriasis can also cause inflammation of the joints, known as psoriatic arthritis. In the U.S. it is estimated that two percent of the population has psoriasis.

SUMMARY

According to one aspect of the present disclosure, a method is disclosed for treating psoriasis. The method comprises the steps of providing a pharmaceutical composition containing at least *Ganoderma lucidum* extract and administering a therapeutically effective amount of the composition to a patient in need thereof.

According to another aspect of the present disclosure, a method is disclosed for treating psoriasis. The method comprises the steps of first purifying *Ganoderma lucidum* extract into at least one fraction, then providing a pharmaceutical composition comprising at least one of the *Ganoderma lucidum* fractions, and administering a therapeutically effective amount of the composition to a patient in need thereof.

A pharmaceutical composition for treating psoriasis is disclosed. The pharmaceutical composition comprises a *Ganoderma lucidum* extract.

A method for alleviating symptoms of psoriasis is disclosed. The method comprises the steps of providing a pharmaceutical composition containing at least *Ganoderma lucidum* extract and administering an amount of the composition effective to increase at least one of an IL-10 and IL-1Ra expression, whereby the symptoms of psoriasis are ameliorated.

DRAWINGS

The above-mentioned features and objects of the present disclosure will become more apparent with reference to the following description taken in conjunction with the accompanying drawings wherein like reference numerals denote like elements. The patent or application file contains at least one drawing executed in color. Copies of this patent or patent application publication with color drawing(s) will be provided by the Office upon request and payment of the necessary fee.

Figure 1B:
Figure 2A:
Figure 2B:

FIG. 1*a* shows a leg of a female patient with psoriasis.
FIG. 1*b* shows the same leg of the female patient 5.5 months after treatment with the pharmaceutical composition.
FIG. 2*a* shows an arm of a male patient with psoriasis.
FIG. 2*b* shows the same arm of the male patient 1 month after treatment with the pharmaceutical composition.

DETAILED DESCRIPTION

The present disclosure relates to pharmaceutical compositions containing *Ganoderma lucidum* extract to treat psoriasis. The methods and compositions address psoriasis treatment as well as prophylaxis and relapse prevention. Thus, the methods and compositions of the present disclosure are appropriate for patients who currently suffer from psoriasis and for patients susceptible to psoriasis relapse.

The phrase "*Ganoderma lucidum*" refers to the *Ganoderma lucidum* fungus, which also includes any tissue, part or fraction therefrom and/or any preparation thereof including homogenates, suspension, filtrates, filtration residues and solution. Other names for *Ganoderma lucidum* include Reishi and Ling-Zhi.

The term "extract" refers to any solid, viscid, and liquid substance obtained through extraction from a given substance. In the present disclosure, a *Ganoderma lucidum* extract includes any solid, viscid, and liquid substance extracted from *Ganoderma lucidum* mushroom tissue.

Various methods and procedures for extraction are known and used by those skilled in the art. Such methods and procedures include both physical and chemical processes, including solvent utilization, distillation, percolation, and supercritical fluid extraction. The extract may be further filtered or concentrated as desired. In one example, a *Ganoderma lucidum* extract is obtained by treating homogenized *Ganoderma lucidum* mushroom tissue with 0.1 N NaOH for a predetermined time.

According to exemplary implementations, the pharmaceutical composition may be in various forms including powders, creams, gels, salves, ointments, solutions, tablets, capsules, sprays, and patches. Vehicles and carriers may be used for delivery of the composition to the patient. Such carriers include solubilizing agents, diluents, and dispersion media. These carriers are biocompatible, pharmaceutically acceptable, and do not alter the treatment characteristics of the extract. Excipients, adjuvants and other ingredients may also be included in the composition.

The composition should be stable during manufacture and storage. The *Ganoderma lucidum* extract or specific constituents of the extract may be encapsulated, with agents such as aluminum monostearate, gelatin, and biodegradable and biocompatible polymers, to prevent undesired degradation in the body or by other ingredients in the composition. Anti-bacteria and anti-fungal agents such as benzyl alcohols, parabens, chlorobutanol, phenol, ascorbic acid, and thimerosal may also be included in the composition.

Psoriasis is a skin disorder characterized by inflammation and abnormal epidermal proliferation. Several studies have observed that T lymphocytes and cytokines play an important role in the pathogenesis of this disease.

According to the present disclosure, a pharmaceutical composition containing *Ganoderma lucidum* extract for treating psoriasis is disclosed. In some exemplary implementations, the *Ganoderma lucidum* extract induces increased IL-10 and/or IL-1Ra expression. The increased expression of IL-10 and IL-1Ra plays a role in the treatment of psoriasis, the role may be at least anti-inflammatory.

Other diseases and inflammatory symptoms associated with decreased IL-10 and/or IL-1Ra expression may also be treated with the composition containing *Ganoderma lucidum* extract. Examples include but are not limited to arthritis, inflammatory bowel diseases, multiple sclerosis and inflammation due to transplantation or viral infections.

In one aspect of the present disclosure, a method is provided for treating psoriasis. The method comprises the steps of providing a pharmaceutical composition containing at least *Ganoderma lucidum* extract and administering a therapeutically effective amount of the composition to a patient in need thereof.

Administration of the composition may be achieved through various methods to different parts of the body, including intravenous, intradermal, subcutaneous, oral (e.g., inhalation), transdermal (i.e., topical), transmucosal, and rectal administration.

Topical administration to a localized area of skin may be achieved with compositions that include creams, gels, ointments, and salves. Polyethylene glycols, propylene glycols, glycerin, and other synthetic solvents may be used in the compositions.

In other exemplary implementations, the composition is a solution or suspension injected parenterally, intradermally, or subcutaneously. Carriers include water, saline solutions, and other synthetic solvents. Buffers such as acetates, citrates, and phosphates may be used, as well agents for adjusting tonicity, such as sodium chloride and dextrose, and agents for adjusting pH, such as hydrochloric acid and sodium hydroxide.

The phrase "therapeutically effective amount" refers to an amount that produces some desired effect at a reasonable benefit/risk ratio applicable to any medical treatment. The effective amount may vary depending on such factors as the disease or condition being treated, the particular targeted constructs being administered, the size of the subject, or the severity of the disease or condition. One of ordinary skill in the art may empirically determine the effective amount of a particular compound without necessitating undue experimentation.

In another aspect of the present disclosure, a method is provided for treating psoriasis. The method comprises the steps of filtering *Ganoderma lucidum* extract into at least one fraction, providing a pharmaceutical composition having at least one of the *Ganoderma lucidum* fractions, and administering a therapeutically effective amount of the composition to a patient in need thereof.

The term "fraction" refers to one of the separable constituents of a substance. The fractions are collected based on differences in a specific property of the individual constituents. In exemplary implementations, the fractions are identified by their respective abilities to absorb light.

The term "filtering" refers to any procedure used to separate a constituent of a substance from other constituents of the substance. Various methods and procedures for filtration are known and used by those skilled in the art. Such methods and procedures include dialysis and gel filtration chromatography. In one example, *Ganoderma lucidum* extract is filtered using a Sephaceryl S-500 column and eluting with a Tris buffer solution to form one or more fractions.

In at least one exemplary implementation of the present disclosure, the *Ganoderma lucidum* fraction, herein referred to as "F3" or "Fraction 3", contains a glycoprotein with fucose residues. In various exemplary implementations, the fucose residues are bound with α-1,2-fucosidic linkages or α-3,4-fucosidic linkages, and may be located terminally, in a region proximate to a free end of a chain of sugars. In further exemplary implementations, the fucose-containing glycoprotein can also comprise of glucose, mannose, N-acetylglucosamine, xylose, and galactose. An amino acid component may also be included, and may comprise modifications that do not adversely alter characteristics of the fucose-containing glycoprotein.

In another aspect of the present disclosure, a method is provided for alleviating symptoms of psoriasis. The method comprises the steps of providing a pharmaceutical composition containing at least *Ganoderma lucidum* extract and administering an amount of the composition effective to increase at least one of an IL-10 and IL-1Ra expression, whereby the symptoms of psoriasis are ameliorated.

EXAMPLE

A more complete understanding of the present disclosure can be obtained by reference to the following specific examples and figures. The examples and figures are described solely for purposes of illustration and are not intended to limit the scope of the disclosure. Changes in form and substitution of equivalents are contemplated as circumstances may suggest or render expedient. Although specific terms have been employed herein, such terms are intended in a descriptive sense and not for purposes of limitations. Modifications and variations of the disclosure as hereinbefore set forth can be made without departing from the spirit and scope thereof, and, therefore, only such limitations should be imposed as are indicated by the appended claims.

Example 1

Effect of F3 on IL-10 and IL-1Ra Cytokine Expression from Mice Spleen Cells

Fresh spleen cells were harvested from BALB/c male mice (12 weeks old), suspended in RPMI-1640 medium containing 10% fetal calf serum and 100 μg/ml Penicillin/Streptomycin ("RPMI Buffer Medium"). The suspension was subjected to centrifugation to remove the supernatant. The cells collected were washed with PBS buffer twice, followed by treatment with KCL Lysis buffer (0.15N $NH_4Cl$, 1 mM $NaHCO_3$, 0.1 mM EDTA) for 10 min to destroy red blood cells. After KCL Lysis buffer treatment, the cells were washed with PBS buffer again. The washed cells were re-suspended in RPMI Buffer Medium and their final concentration was adjusted to $1\times10^6$ cells/mL in the same RPMI Buffer Medium. Sterile F3 solution was prepared by dissolving F3 in RPMI Buffer Medium at a concentration of 200 ppm, followed by sterile filtration through 0.22 micron membrane before use. Equal volume of Sterile F3 solution and cell suspension was mixed to make F3 final concentration at 100 ppm. For control without F3, the F3 solution was replaced with RPMI Buffer Medium. The cell suspensions with or without F3 were incubated at 37° C. under 5% $CO_2$ for 24 hours. The culture supernatant was collected; IL-10 and IL-1Ra levels in supernatant were determined by enzyme-linked immunosorbent assay (ELISA) kit according to the manufacturer's instructions (R&D Systems, MN, U.S.A.)

TABLE 1

IL-10 and IL-1Ra expression of mouse splenocytes ($5 \times 10^5$ cells/mL) treated with F3 (100 ppm).

| Groups | Expression of Cytokines | |
|---|---|---|
| | IL-10 (pg/mL) | IL-1Ra (pg/mL) |
| Control, n = 3 | 59.6 ± 5.8 | 867.8 ± 55.2 |
| F3 (100 ppm), n = 3 | 925.4 ± 20.1 | 2392.4 ± 35.1 |

The results from Table I above indicate F3 can stimulate IL-10 and IL-1Ra cytokine expression from mice spleen cells.

Example 2

Effect of F3 Treatment on Serum Level of IL-10 and IL-1Ra Cytokines of BALB/c Mice Six-week-old male BALB/c mice were purchased from BioLASCO Taiwan Co., Ltd. Sterile F3 solution for injection was prepared by dissolving F3 in phosphate buffer saline (PBS) at a concentration of 132 mg/ml, followed by sterile filtration through 0.22 micron membrane before use. Mice were intraperitoneal administrated with 0.1 ml F3 solution (approx. 660 mg/Kg body weight) or 0.1 ml of PBS (control group); 1 and 3 hours after injection of either F3 or PBS solution, the mice were bled from submandibular vein. Cytokine IL-10 and IL-1Ra levels in the plasma were determined by enzyme-linked immunosorbent assay (ELISA) kit according to the manufacturer's instructions (R&D Systems, Minn., U.S.A.).

TABLE 2

Effect of F3 treatment on serum level of IL-10 and IL-1Ra cytokines of BALB/c mice (n = 20).

| Time after F3 or PBS Treatment (hour) | Group | Cytokine Concentration in Plasma | |
|---|---|---|---|
| | | IL-10 (pg/ml) | IL-1Ra (pg/ml) |
| 1 | Control | 86.7 ± 7.3 | 235.3 ± 60.9 |
| | F3 | 301.5 ± 69.5* | 326.5 ± 70.0 |
| 3 | Control | 90.0 ± 8.2 | 365.5 ± 163.1 |
| | F3 | 162.6 ± 15.2* | 3662.8 ± 398.9* |

Data represents mean ± SD (n = 20).
*$P < 0.05$ compared to control mice.

The results in Table 2 indicate within 1 and 3 hours after treatment by F3, BALB/c mice exhibit significant increase in serum cytokine IL-10 and IL-1Ra level. Current findings demonstrate that F3 alters the expression of the serum cytokine level associated with psoriasis symptoms.

Example 3

Effect of F3 Treatment on Psoriasis Patients

Two patients with psoriasis were given F3 capsules to be taken orally twice a day, once in the morning and once in the evening. Each F3 capsule contained 175 mg of F3 as well as excipients and other inert materials. FIG. 1a shows the leg of a female patient before taking F3. FIG. 1b shows the same leg of the female patient 5.5 months after taking the F3 capsules. FIG. 2a shows the arm of a male patient before taking F3. FIG. 2b shows the same arm of the male patient 1 month after taking the F3 capsules. Improvements on both the female and male patients' skin were noticeable following F3 treatment.

While the method and agent have been described in terms of what are presently considered to be the most practical and preferred implementations, it is to be understood that the disclosure need not be limited to the disclosed exemplary implementations. It is intended to cover various modifications and similar arrangements included within the spirit and scope of the claims, the scope of which should be accorded the broadest interpretation so as to encompass all such modifications and similar structures. The present disclosure includes any and all implementations of the following claims.

The invention claimed is:

1. A method for treating psoriasis, the method comprising
    providing a pharmaceutical composition containing at least a sodium hydroxide (NaOH) extract of *Ganoderma lucidum*; and
    administering a therapeutically effective amount of the composition to a patient in need thereof to increase IL-10 expression in the patient.

2. The method of claim 1 wherein said composition is administered intravenously, intradermally, subcutaneously, orally, transdermally, transmucosally, or rectally.

3. The method of claim 1 wherein said composition is formulated as a cream, gel, salve, ointment, solution, tablet, capsule, spray, or patch.

4. A method for treating psoriasis comprising
    providing a NaOH extract of *Ganoderma lucidum*;
    purifying the *Ganoderma lucidum* extract into at least one fraction;
    providing a pharmaceutical composition comprising at least one *Ganoderma lucidum* fraction; and
    administering a therapeutically effective amount of the composition to a patient in need thereof wherein the fraction increases IL-10expression in the patient.

5. The method of claim 4 wherein said composition is administered intravenously, intradermally, subcutaneously, orally, transdermally, transmucosally, or rectally.

6. The method of claim 4 wherein said composition is formulated as a cream, gel, salve, ointment, solution, tablet, capsule, spray, or patch.

7. The method of claim 4 wherein said fraction comprises at least one fucose-containing glycoprotein.

8. A method for alleviating symptoms of psoriasis, the method comprising
    providing a pharmaceutical composition containing at least a NaOH extract of *Ganoderma lucidum*; and
    administering an amount of the composition effective to increase IL-10expression to a subject with psoriasis, whereby the symptoms of psoriasis are ameliorated.

9. The method of claim 8, further comprising:
    fractionating the NaOH extract prior to administration, wherein the fraction comprises at least one fucose-containing glycoprotein.

10. The method of claim 8 wherein said composition is administered intravenously, intradermally, subcutaneously, orally, transdermally, transmucosally, or rectally.

11. The method of claim 8 wherein said composition is formulated as a cream, gel, salve, ointment, solution, tablet, capsule, spray, or patch.

* * * * *